(12) United States Patent
Gerndt et al.

(10) Patent No.: US 7,263,161 B2
(45) Date of Patent: Aug. 28, 2007

(54) ANALYSIS DEVICE WITH VARIABLY ILLUMINATED STRIP DETECTOR

(75) Inventors: Ekkehard Gerndt, Karlsruhe (DE); Pawel Grybos, Rzaska (PL); Lutz Bruegemann, Durmersheim (DE); Rachel Eisenhower, Karlsruhe (DE); Arne Kasten, Karlsruhe (DE)

(73) Assignee: Bruker AXS GmbH, Karlsruhe (DE)

( * ) Notice: Subject to any disclaimer, the term of this patent is extended or adjusted under 35 U.S.C. 154(b) by 0 days.

(21) Appl. No.: 11/236,651

(22) Filed: Sep. 28, 2005

(65) Prior Publication Data

US 2006/0083350 A1    Apr. 20, 2006

(30) Foreign Application Priority Data

Oct. 16, 2004   (DE) ................. 10 2004 050 543

(51) Int. Cl.
*G01N 23/20*   (2006.01)

(52) U.S. Cl. .............. 378/70; 378/71; 378/86
(58) Field of Classification Search ........... 378/70, 378/71, 73, 82, 86, 88, 147, 154, 155, 156, 378/157, 158, 159
See application file for complete search history.

(56) References Cited

U.S. PATENT DOCUMENTS

| | | | |
|---|---|---|---|
| 5,195,115 A | 3/1993 | Schiller | 378/86 |
| 5,231,652 A | 7/1993 | Harding | 378/86 |
| 5,394,453 A | 2/1995 | Harding | 378/86 |
| 5,428,657 A | 6/1995 | Papanicolopoulos | 378/73 |
| 5,446,777 A * | 8/1995 | Houtman | 378/45 |
| 2002/0053641 A1 | 5/2002 | Verbruggen | 250/370.09 |
| 2003/0075684 A1 | 4/2003 | Takami | 250/310 |
| 2005/0105684 A1* | 5/2005 | Bruegemann et al. | 378/71 |

FOREIGN PATENT DOCUMENTS

| | | |
|---|---|---|
| DE | 102 26 828 | 12/2003 |
| DE | 102 37 546 | 3/2004 |
| EP | 0 358 965 | 3/1990 |
| WO | WO96/24863 | 8/1996 |
| WO | WO96/38722 | 12/1996 |
| WO | WO98/33062 | 7/1998 |

* cited by examiner

Primary Examiner—Courtney Thomas
(74) Attorney, Agent, or Firm—Paul Vincent

(57) ABSTRACT

An X-ray or neutron-optical analysis device comprising means for directing radiation from a source (1) onto a sample (2), and a detector (7) with n substantially identical detector elements ($D_i$) which are disposed parallel, next to each other in a first direction x and which extend in strips in a second direction y, wherein i=1, . . . n, for one-dimensional spatially-resolved detection of radiation reflected, scattered or diffracted by the sample (2) onto the detector (7), and with a detection electronics for processing the detector signals of the n detector elements ($D_i$), wherein the detection electronics can reliably process a maximum radiation intensity per detector element ($D_i$) without overloading, is characterized in that an optical element is disposed in front of the detector (7) which covers or weakens radiation incident on the surfaces of the respective n detector elements ($D_i$) in correspondence with a predetermined, non-constant transmission function f(x) and/or the optical element comprises a collimator (6) which can be displaced along the strip direction y. The inventive analysis device permits artificial enlargement of the dynamic range of the detector (7).

19 Claims, 2 Drawing Sheets

ANALYSIS DEVICE WITH VARIABLY ILLUMINATED STRIP DETECTOR

This application claims Paris Convention priority of DE 10 2004 050 543.8 filed Oct. 16, 2004 the complete disclosure of which is hereby incorporated by reference.

BACKGROUND OF THE INVENTION

The invention concerns an X-ray or neutron-optical analysis device with means for directing radiation from a source onto a sample and with a detector having n substantially identical detector elements $D_i$ which are disposed parallel to each other in a first direction, and which extend in strips in a second direction y, wherein i=1, ... n, for one-dimensional spatially-resolved detection of radiation reflected, scattered or diffracted by the sample onto the detector, and comprising a detection electronics for processing the detector signals of the n detector elements $D_i$, wherein the detection electronics reliably processes a maximum defined radiation intensity per detector element $D_i$ without overloading.

An X-ray analysis device of this type is disclosed in US 2002/0053641.

Scattering, diffraction and reflection of X-ray and neutron radiation are important methods for analyzing a structure. The diffraction of X-ray or neutron radiation can give e.g. information concerning the symmetry properties of the scattering (generally crystalline) material.

The detector disclosed in US 2002/0053641 has an array of adjacent strip-shaped detector elements for detecting the angle at which the radiation leaves the sample, relative to the incident beam. This permits one-dimensional spatially resolved acquisition of diffracted or scattered X-ray radiation. The location of a detector element is thereby a measure of the angular deflection of the radiation leaving the sample. Acquisition of spatially resolved intensity distributions (diffractograms) using such a device can therefore provide information about the lattice structure of the sample. In particular, for measurements performed with grazing incidence X-ray radiation, e.g. XRR measurements (x-ray reflection), the intensity within the acquired X-ray diffractogram decreases exponentially with distance such that the intensity region of the entire diffractogram extends over several orders of magnitude. Since the different detector elements are correspondingly illuminated with different intensities, the acquisition of X-ray diffractograms requires detectors having a very high dynamic range (several orders of magnitude). Conventional detectors become saturated at very high count rates and these regions provide no useful information. The effective, useful range of these conventional detectors is therefore limited.

A collimator is conventionally disposed in front of a one-dimensional detector during medical X-ray transmission measurements to block radiation in defined regions of the detector elements. Essentially only one shadow image is measured in this case. An arrangement of this type is described e.g. by A. Cabal et al. "Feasibility of silicon strip detectors and low noise multichannel readout system for medical digital radiography." 6th Mexican Symposium on Medical Physics, Mexico, Mexico City, March 2002, American Institute of Physics Conference Proceedings, no 630, 2002, pp. 202-207, USA.

It is the object of the present invention to propose an X-ray or neutron-optical analysis device for detecting reflected, scattered or diffracted radiation which largely eliminates or at least reduces overloading of the detector elements.

SUMMARY OF THE INVENTION

This object is achieved in accordance with the invention in that an optical element is disposed in front of the detector which covers or weakens part of the radiation incident on the surfaces of the n detector elements (Di) according to a predetermined, non-constant transmission function f(x) and/or the optical element comprises a collimator which can be displaced along the strip direction y.

An optical element with a non-constant transmission function f(x) can reduce the optical permeability in the region of certain detector elements compared to other detector elements to prevent saturation of individual detector elements. In a similar manner, a collimator which can be displaced in the y direction can collimate out radiation from certain regions within one detector element. The detected radiation is confined to a region Δy of the respective detector elements, to also prevent detector element overloading.

The inventive analysis device is used e.g. for at least one-dimensional x-direction-dependent detection of radiation, incident on a detector in an analysis device, whose intensity changes as a function of x, and whose envelope, i.e. the line joining the intensity maxima, is roughly known from a preliminary measurement etc. For a measurement, an optical element having a transmission function f(x) and optionally a grey filter with an attenuation k are selected to collimate out/attenuate radiation for each detector element in such a manner that the envelope of the intensity change l(x) does not overload the detection electronics, and the transmission function f(x), integrated over each of the n detector elements $D_i$ and optionally the attenuation k are taken into consideration in determining a true intensity dependence of the radiation l(x).

To exactly determine the true intensity behavior of the radiation l(x), it has turned out to be advantageous to consider deviations from linearity of the characteristic lines of the detector elements.

In a particularly advantageous manner, the intensities associated with the n detector elements $D_i$ are calculated according to individually differing characteristic lines.

In the inventive analysis device, the radiation from the sample incident on the detector has an intensity distribution l(x) which varies over at least one order of magnitude, preferably several orders of magnitude. In particular, it is a diffractogram of the sample. The advantages of the invention can be utilized with particular preference in this case, since the dynamic range of conventional detectors is often insufficient for diffractograms whose intensity distribution l(x) varies over several orders of magnitude.

In a preferred embodiment of the inventive analysis device, the transmission function f(x) monotonically increases in the x direction to a maximum value $f_{max}$, wherein, in particular, $f_{max}=1$. In this manner, the full radiation intensity is detected at suitable locations of the detector.

The transmission function f(x) is preferably selected to substantially follow the inverse of the envelope of an intensity distribution to be expected, in particular, a diffractogram l(x). The radiation transmission is thereby selected to be high in regions with little expected radiation intensity and correspondingly low in regions with expected high radiation intensities to obtain maximum yield of detected radiation without saturating the detector.

In one possible embodiment of the inventive analysis device, an additional grey filter is provided which integrally weakens the overall intensity of the radiation incident on the detector by a factor k.

In a further embodiment, the optical element is partially transparent and partially impermeable to radiation. An optical element of this type may be provided e.g. in the form of a collimator, in particular, a gap which permits complete collimation of individual detector elements or part of individual detector elements.

A preferred embodiment of the analysis device comprises a wedge filter in the x direction as the optical element to facilitate monotonic increase of the radiation permeability of the optical element.

In a particularly advantageous embodiment of the analysis device, the optical element comprises a gap in the x direction which can be displaced in the y direction. The optical element can be displaced at least once in the y direction after a measurement, and the measurement can be repeated and accumulated. In this manner, the entire detector region can be scanned and the overall intensity can be determined without exceeding the dynamic range of the detector.

After a measurement, the optical element is displaced e.g. at least (j−1) times (j>1) in the y direction and the measurement is repeated (j−1) times, thereby obtaining a two-dimensional intensity behavior of the radiation l(x,y) with n measured values in the x direction and j measured values in the y direction.

The present analysis device can be further advantageously used for one-dimensional, spatially dependent detection in the y direction of radiation incident on the detector using the inventive analysis device having an intensity as a function of x and y with a behavior whose envelope, i.e. the line connecting the intensity maxima, is roughly known from a preliminary measurement etc. A collimator gap width and optionally a grey filter of attenuation k are selected for a measurement in such a manner that the radiation is collimated out/weakened for each detector element such that the envelope of the intensity behavior l(x,y) does not overload the detection electronics. During or after the measurement, the intensities of the n detector elements $D_i$ are accumulated, the collimator is displaced at least once in the y direction and the measurement and accumulation are repeated.

A particularly advantageous embodiment utilizes a gap having a width which is small compared to the separation between neighboring detector elements ($D_i$), in particular, smaller than half the separation. This permits detection of only part of the radiation incident on the detector element, thereby increasing the spatial resolution.

In a special embodiment of the invention, the optical element comprises two blades which can be separately displaced. A gap with varying separation can thereby be realized in dependence on the application.

In a further embodiment of the inventive analysis device, the optical element has transparent regions of different numbers and/or sizes which are distributed over the detector surface in the region of at least some of the n detector elements ($D_i$). Regions which are of interest for special applications can thereby be precisely selected and regions of no interest can simultaneously be collimated out.

In a particularly advantageous manner, the analysis device comprises several optical elements which can be mutually exchanged and/or combined with each other. The analysis device may then be used for different applications.

For particularly sensitive measurements, the detector and the detection electronics advantageously register and count the incidence of individual radiation quanta on the detector elements ($D_i$). This can be realized e.g. using an individual photon detector.

The invention can be utilized with particular advantage if the angle between the radiation incident on and emerging from the sample is between 165° and 180°, since measurements in such angular ranges, which are also called "grazing incidence" measurements, have very high intensity changes in small angular regions.

In particular, for GISAXS (grazing incidence small angle x-ray scattering), the detector can preferably be rotated about an axis perpendicular to the detector surface. The detector path can thereby traverse a circular surface perpendicular to the scattering direction having a diameter of at least the length of the detector path. If the center of rotation is selected to be at one end of the detector path, the diameter of the circular surface may be up to twice the length of the detector. The one-dimensional, rotatably disposed detector thereby becomes a virtual two-dimensional detector. If the collimator used has a smaller opening than the granularity of the detector, it is also possible to improve the spatial resolution in any direction.

The inventive analysis device may also be used as a point detector (0-D detector) by adding the detected radiation intensities of the individual detector elements detected by the detection electronics. Conventional fast 0-D detectors (up to $10^8$ cps (counts per second)) have a relatively small sensitive surface (approximately 3 mm×5 mm). The inventive analysis device, however, realizes a 0-D detector which has a high count rate of up to $2 \times 10^8$ cps and at the same time a sensitive surface of up to 15 mm×15 mm. This can be realized with silicon drift chambers e.g. only with high technical and financial expense.

Further advantages of the invention can be extracted from the description and the drawing. The features mentioned above and below may be used individually or collectively in arbitrary combination. The embodiments shown and described are not to be understood as exhaustive enumeration but have exemplary character for describing the invention.

BRIEF DESCRIPTION OF THE DRAWING

FIG. 1b shows a schematic top view of an inventive analysis device of FIG. 1a;

DESCRIPTION OF THE PREFERRED EMBODIMENT

Figure 1A:
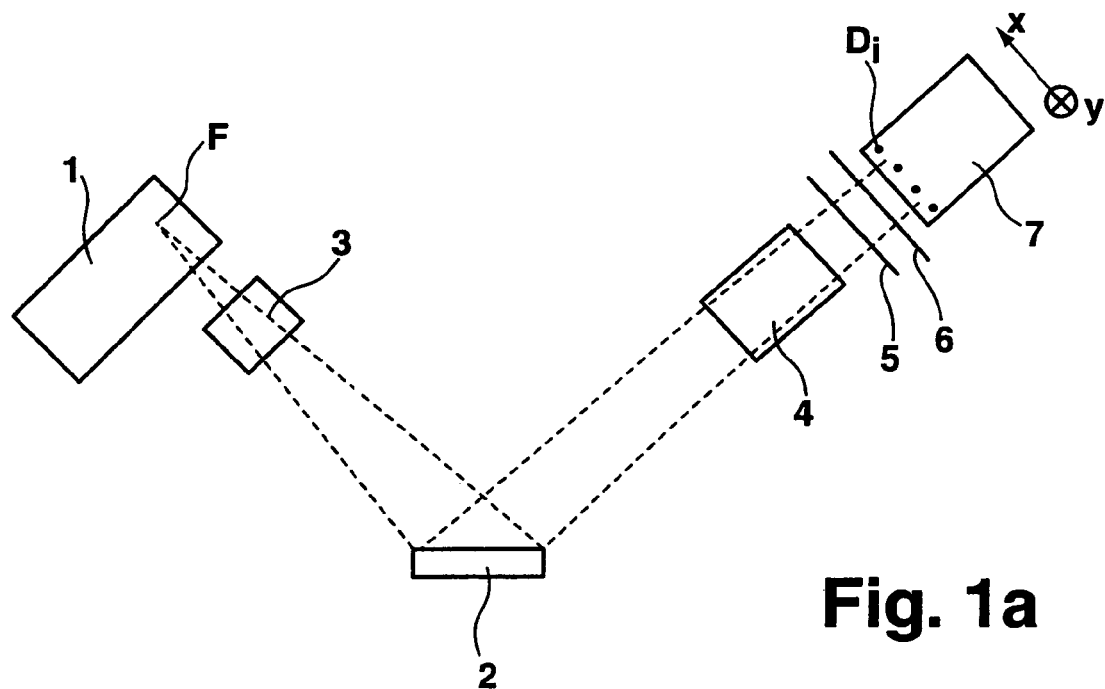
FIG. 1a shows a schematic side view of an inventive analysis device.
Figure 1B:
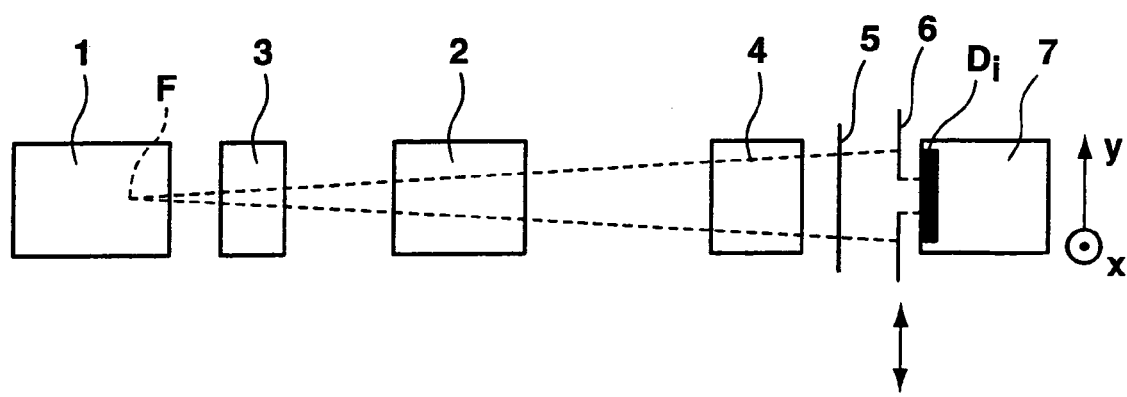

FIGS. 1a and 1b show a side view and a top view of an inventive analysis device. A source 1 emits radiation which is directed onto a sample 2. The source 1 may thereby be part of the analysis device, e.g. a conventional X-ray source, or could also be an externally installed source, such as e.g. a synchrotron. A primary optics 3 is disposed in front of the X-ray source 1. It may contain crystals, mirrors or other components which monochromatize the X-ray radiation. Monochromatic radiation is often, but not necessarily used for measuring methods such as XRR (X-ray reflection), GID (Grazing incidence diffraction), GISAXS (grazing incidence small angle x-ray scattering) and may have varying bandwidths. Moreover, the primary optics 3 may comprise monochromator mirrors/crystals and a slot system. After passing the primary optics 3, the radiation is incident on the sample 2 where it is reflected, scattered or diffracted. The radiation emitted by the sample 2 passes an optical device 4 and is incident on one or more optical elements. In the embodiment of FIG. 1, the radiation passes through a filter 5 and a gap 6, which can be moved in the y direction, before being detected in a strip detector 7.

For measurements in the Bragg-Brentano geometry, the arrangement of FIG. 1 must be changed such that the focus F of the source 1 and the collimator 6 are located on a circle (the focussing circle) in front of the detector 7. For parallel geometry applications which are used for many measuring methods, this is however not desired. To avoid overloading of the detector 7 due to high radiation intensity, the radiation is collimated out or weakened by the optical elements in selected regions, preferably regions where high radiation intensity is expected. The attenuation factor of the optical elements used can give information about the actual radiation intensity without overloading the detector 7.

Figure 2:
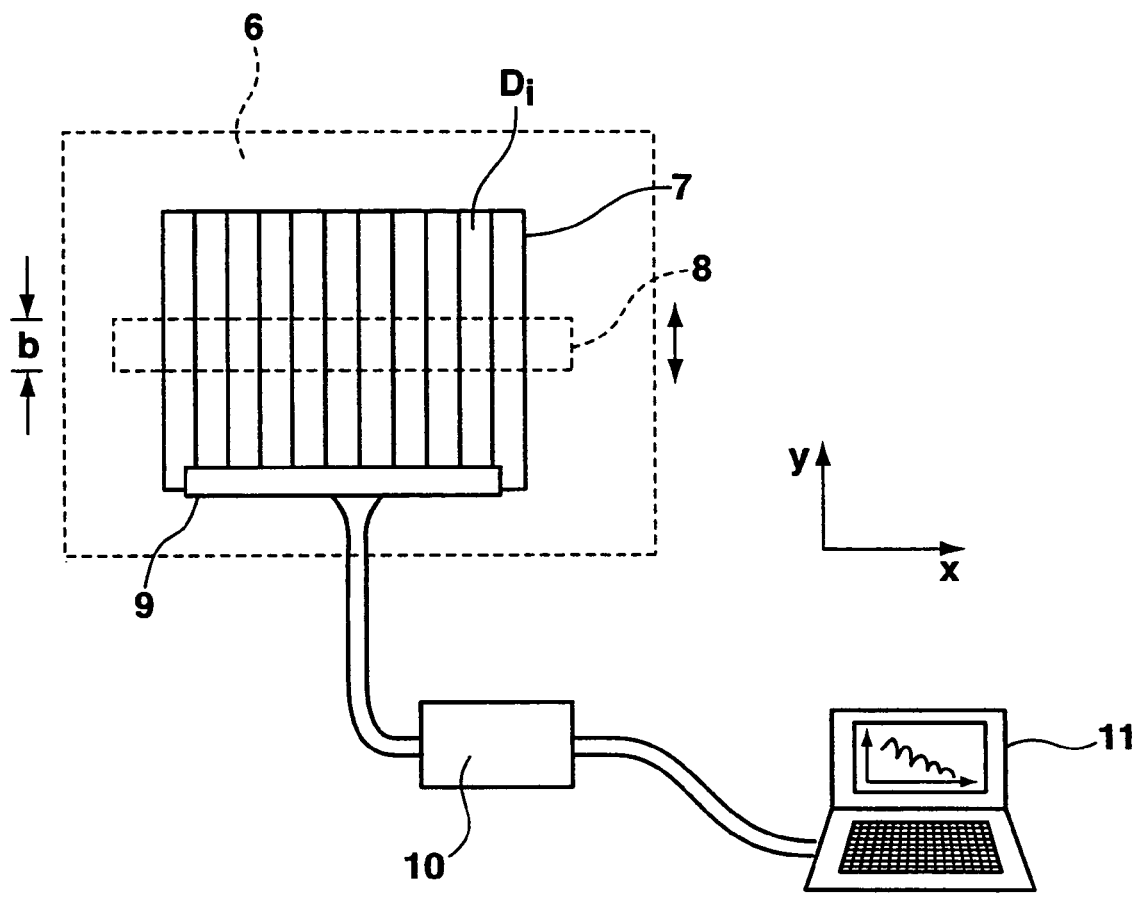
FIG. 2 shows a schematic view of an experimental detector and evaluation electronics construction.

The radiation can be collimated out in certain regions through the arrangement as shown in FIG. 2. FIG. 2 shows a detector 7 with n substantially identical detector elements $D_i$ which are disposed parallel, next to each other in the x direction and extend as strips in a second, y direction. An optical element (broken lines) in the form of a collimator 6 is disposed in front of the detector and can be displaced along the strip direction y, having a gap opening 8 and gap width b. A region $\Delta y$ of width b of the detector elements $D_i$ in which the incident radiation is detected can be selected by the displaceable collimator 6. The radiation incident on the detector elements $D_i$ generates electron-hole pairs. The electrons are collected in a read-out means 9 and passed to an evaluation means 10. After evaluation, the detected radiation intensity can be displayed in the form of a diffractogram on a computer display 11. The radiation incident outside the gap opening 8 is thereby collimated out. Through suitable displacement of the collimator 6, the entire surface of each detector element $D_i$ can be successively "scanned" and the overall intensity of the radiation incident on the detector element $D_i$ can be determined through summation of the values measured for a detector element $D_i$. Overloading of the detector due to excessive radiation intensity is thereby prevented. The count rate which can be effectively obtained can be extended up to several orders of magnitude through splitting the measurement into many measuring steps.

Since the values determined in the described individual measurements are associated with a certain region in the y direction in dependence on the position of the collimator, and therefore also contain information which is spatially resolved in the y direction, a two-dimensional diffractogram which is additionally resolved in the y direction can be produced through suitable displacement of the collimator 6. In this manner, the inventive analysis device permits acquisition of two-dimensional diffractograms using a one-dimensional detector 7.

This is particularly advantageous for investigating whether a powder sample unexpectedly contains textures. Each detector is thereby used as a one dimensional position sensitive detector (PSD) with a two-dimensional image being acquired during the investigation. It is used to measure the structure of the Debye rings, obtaining corresponding information which could influence the measurement parameters for the subsequent investigations of the sample. The invention is advantageous in that occasional 2-dimensional measurements are possible in a straightforward manner. A more complex detector (sensor) for the second dimension and associated electronics is not necessary.

A further field of application of the inventive analysis device are topographical measurements using X-rays. These are used to find crystal defects, e.g. in the semi-conductor industry. This also requires two-dimensional read-out which can be provided with simple technical means using the invention. The invention is very suitable for occasional measurements, since the measuring assembly can be easily combined with an XRR-, GID-, GISAXS assembly. This can be of interest to the user.

If a collimator is selected having a gap width b which is smaller than the granularity of the detector 7, the spatial resolution of the diagram acquired with this arrangement can be improved compared to the resolution of the detector 7 itself.

Figure 3:
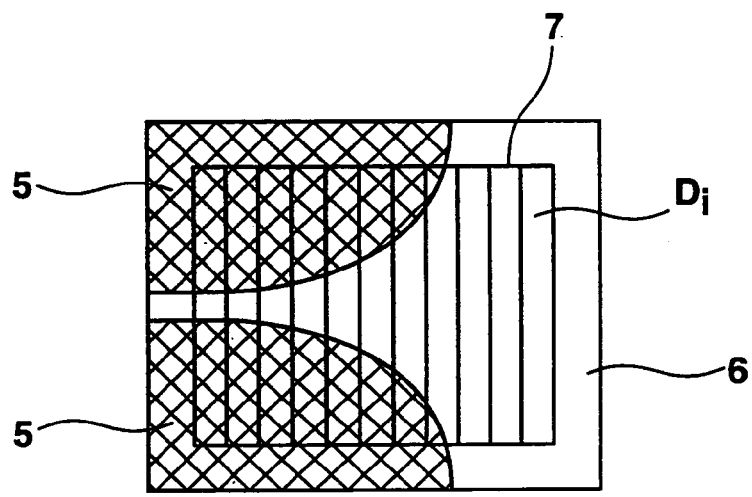
FIG. 3 shows an exemplary view of a gap disposed in front of the detector elements.

FIG. 3 shows a section of a strip detector 7 with collimator 6 and filter 5 disposed in front of it. The collimator 6 limits the region of incidence of the radiation emitted by the sample 2 in the y direction as described above in connection with FIG. 2. The regions of the detector elements $D_i$ which are exposed in the region of the gap opening 8 of the collimator 6, are additionally covered by a filter 5, wherein the filter 5 has a non-constant transmission function f(x) in the x direction, thereby collimating out or weakening the incident radiation in additional regions within the gap opening 8 of the collimator 6. The filter 5 may e.g. be a wedge filter with continuously changing transmission function. The transmission function f(x) is selected with particular preference to substantially follow the inverse of the envelope of an intensity distribution l(x) to be expected. Other filter arrangements are, however, also feasible.

In the FIG. 3 embodiment of the filter 5, the transmission function is not constant in the x or y directions ($f(x) \neq const.$, $f(y) \neq const.$). As a result of the non-constant transmission function in the y direction, only part of the individual detector elements $D_i$ is exposed to incident radiation (similar to the collimator 6) and/or the radiation is weakened in certain regions.

The main fields of application of the inventive analysis device which offer excellent utilization of the invention are, in particular, but not exclusively X-ray reflection (XRR), grazing incidence diffraction (GID) and grazing incidence small angle X-ray scattering (GISAXS).

The three mentioned methods are often used in combination with each other for examining the surface structure for nanoscale material samples, typically for so-called "thin films". The "surface" thereby defines the uppermost material layers up to a depth of 2 μm or more. XRR examines the properties at right angles to the surface such as layer thickness, material composition and roughness. GID measures the lateral structure, GISAXS measures the mesoscopic material properties parallel and at right angles to the macroscopic surface. These methods are mainly used for the study of new materials in the nanotechnology and semiconductor industries.

In the above-mentioned measuring methods, the X-ray angle of incidence $\alpha_i$, i.e. the angle between incident X-rays and lattice plane of the sample 2 is close to and below the critical angle $\alpha_c$, the angle of total external reflection of the X-rays. The value of $\alpha_c$ depends on the X-ray radiation wavelength and on the material properties. A typical value of $\alpha_c$ is between 0.2° and 0.6° for common materials with copper $K_\alpha$ X-ray radiation. The angle of incidence must be precisely adhered to in these measurements ($\Delta\alpha_i/\alpha_c < 0.05$). Moreover, the intensity of the radiation emitted by the sample 2 must be precisely determined as a function of the angle of emergence in the scattering plane (XRR, GISAXS) and as a function of the axial angle of emergence (GID, GISAXS). This measurement with very high angular granularity (e.g. 0.005°) must furthermore measure intensities of very large intensity bandwidths (dynamic range up to $10^8$ for molten X-ray tubes) and very large values (up to ≈10⁸ cps for molten X-ray tubes) must be measured. The inventive analysis device artificially extends the insufficient dynamic range of the measuring apparatus but does not change the background noise (lowest measurable count rate) to thereby permit direct measurements (e.g. XRR).

For GISAXS, the required angular resolution in the axial angular direction can be provided by conventional means (e.g. strip detector separation 50 μm with digital read-out). The scattering plane requires a considerably higher (by a factor of 2 to 3) angular resolution, which can be realized with the inventive analysis device. CCD detectors have, by nature, a higher granularity than strip detectors, but also a considerably higher base noise. Since CCD detectors integrate, they cannot detect individual photons. However, this detector property is required for GISAXS measurements.

Individual photon detection is also required for simple small angle scattering measurement (SAXS) in transmission by measuring a 2-dimensional image along the strips by displacing a collimator transverse to the strips. The signal intensities of transmission SAXS measurements are typically very weak. The inventive construction advantageously offers the possibility of individual photon detection. Moreover, 2-dimensional acquisitions may also be advantageous for this method.

The inventive analysis device permits acquisition of one-dimensional and also two-dimensional diffractograms using a conventional one-dimensional strip detector 7, as well as artificial enlargement of the dynamic range of the detector 7 in addition to individual photon detection. At the same time, the inventive analysis device also permits improvement in the spatial resolution, beyond the granularity of the detector elements.

LIST OF REFERENCE NUMERALS b gap width
$D_i$ detector elements
1 source
2 sample
3 primary optics
4 optical device
5 filter
6 collimator
7 detector
8 gap opening
9 read-out means
10 evaluation means
11 computer display

We claim:

1. An X-ray or neutron optical analysis device for measuring a sample, the device comprising:
   a radiation source;
   a radiation detector, said detector having a plurality of substantially identical, separate detector elements disposed parallel to and adjacent to each other in a first x-direction and extending as strips in a second y-direction, orthogonal to said x-direction, to provide one-dimensional spatially resolved detection in said x-direction of radiation reflected, scattered or diffracted by the sample;
   a detection electronics for processing detector signals from each of said plurality of detector elements, said detection electronics having a maximum radiation intensity per detector element which is reliably processed without overloading; and
   an optical element disposed upstream of said detector to reduce radiation intensity incident on surfaces of said detector elements, said optical element comprising a filter structured to produce a transmission function f(x) which changes in said x-direction and/or a collimator which is structured for displacement relative to said radiation detector along said y-direction.

2. The analysis device of claim 1, wherein the radiation emitted from the sample onto said detector has an intensity distribution l(x) which varies over at least one order of magnitude.

3. The analysis device of claim 2, wherein said intensity distribution varies over several orders of magnitude or is a diffractogram of the sample.

4. The analysis device of claim 1, wherein said transmission function f(x) increases monotonically in said x-direction to a maximum value $f_{max}$.

5. The analysis device of claim 4, wherein $f_{max}=1$.

6. The analysis device of claim 2, wherein said transmission function f(x) is selected to substantially follow an inverse of an envelope of an expected intensity distribution.

7. The analysis device of claim 6, wherein said expected intensity distribution is a diffractogram.

8. The analysis device of claim 1, further comprising a filter which integrally weakens an overall intensity of the radiation incident on said detector by a factor k.

9. The analysis device of claim 1, wherein said optical element is partially transparent and partially impermeable to the radiation.

10. The analysis device of claim 1, wherein said optical element comprises a wedge filter in said x-direction.

11. The analysis device of claim 1, wherein said optical element has a gap in said x-direction which is structured for displacement in said y direction.

12. The analysis device of claim 11, wherein said gap has a width which is small compared to a separation between neigboring detector elements or which is smaller than half said separation.

13. The analysis device of claim 1, wherein said optical element comprises two blades which are structured for separate displacement thereof.

14. The analysis device of claim 1, wherein said optical element has transparent regions of varying number and/or size distributed over a detector surface in a region of at least some of said n detector elements.

15. The analysis device of claim 1, wherein said optical element comprises a plurality of individual elements which are mutually replaced and/or combined with each other.

16. The analysis device of claim 1, wherein said detector and said detection electronics register and count an incidence of individual radiation quanta on said detector elements.

17. The analysis device of claim 1, wherein an angle between radiation incident on the simple and radiation emerging from the sample is between 165° and 180°.

18. The analysis device of claim 1, wherein said detector is structured for rotation about an axis perpendicular to a detector surface.

19. The analysis device of claim 1, wherein the analysis device comprises means for constructing a point detector (0-D detector) by adding radiation intensities of individual said detector elements detected by said detection electronics.

* * * * *